United States Patent [19]

Wall

[11] 4,144,401

[45] Mar. 13, 1979

[54] ALCOHOL PRODUCTION

[75] Inventor: Robert G. Wall, Pinole, Calif.

[73] Assignee: Chevron Research Company, San Francisco, Calif.

[21] Appl. No.: 898,353

[22] Filed: Apr. 21, 1978

Related U.S. Application Data

[63] Continuation-in-part of Ser. No. 734,688, Oct. 21, 1976, abandoned.

[51] Int. Cl.² ............ C07C 31/04; C07C 31/20
[52] U.S. Cl. ................................. 568/840; 568/852
[58] Field of Search ..................... 568/840, 852

[56] References Cited

U.S. PATENT DOCUMENTS

| | | | |
|---|---|---|---|
| 2,451,333 | 10/1948 | Gresham et al. | 568/852 |
| 3,833,634 | 9/1974 | Pruett et al. | 260/449 R |
| 3,940,432 | 2/1976 | Walker et al. | 260/449 R |

Primary Examiner—Howard T. Mars
Attorney, Agent, or Firm—D. A. Newell; John Stoner, Jr.

[57] ABSTRACT

Ethylene glycol and methanol are prepared in one step by contacting carbon monoxide, hydrogen and formaldehyde in the presence of an alcohol solvent and a catalyst comprising a rhodium compound.

4 Claims, No Drawings

ALCOHOL PRODUCTION

CROSS-REFERENCE TO RELATED APPLICATION

This application is a continuation-in-part of U.S. application Ser. No. 734,688, filed Oct. 21, 1976 now abandoned.

BACKGROUND OF THE INVENTION

The process of this invention is used to prepare ethylene glycol and methanol. More particularly, the process prepares ethylene glycol and methanol in one step from carbon monoxide, hydrogen and formaldehyde under moderate reaction conditions using a catalyst comprising a rhodium compound.

Ethylene glycol is an important industrial alcohol known primarily for its use as an organic solvent and nonvolatile antifreeze or coolant. It is currently produced by a variety of methods. On a commercial scale most ethylene glycol is produced by hydrolysis of ethylene oxide with dilute sulfuric acid, or with water, at high temperature.

In yet another process ethylene glycol is produced by the high temperature, high pressure reaction of carbon monoxide and hydrogen. For example, German Pat. No. 2,426,495 describes a process for producing ethylene glycol and methanol by the metal-carbonyl-catalyzed reaction of hydrogen and carbon monoxide at high pressures and temperatures.

U.S. Pat. No. 2,451,333 granted Oct. 12, 1948 and German Pat. No. 875,802 illustrate the conventional two-step hydroformylation and reduction of formaldehyde. According to the disclosures, hydroformylation of formaldehyde using a cobalt catalyst yields a mixture of acetals and acetaldehyde, which can be reduced to ethylene glycol and ethylene glycol ethers. When the reaction is carried out in an alcohol solvent, the major product is the glycol ether.

The prior art has relied upon harsh reaction condition or multiple step processes to prepare ethylene glycol usually with the formation of by-products such as ethers. Accordingly, a one-step process which can be conducted under moderate conditions without excessive formation of by-products is desirable.

SUMMARY OF THE INVENTION

It has now been discovered that a mixture of ethylene glycol and methanol can be produced by contacting formaldehyde, carbon monoxide and hydrogen in the presence of an alcohol solvent and a catalyst comprising a rhodium compound at a temperature of from about 100° C. to about 200° C. and a pressure of from about 1000 psi to about 10,000 psi. Ethylene glycol is readily separated from the reaction product mixture.

DETAILED DESCRIPTION OF THE INVENTION

The process of this invention provides a one-step process for preparing a glycol-rich mixture of ethylene glycol and methanol under moderate reaction conditions. The process is based upon the finding that carbon monoxide, formaldehyde and hydrogen can be combined under moderate reaction conditions to produce ethylene glycol and methanol by using an alcohol solvent and a catalyst comprising a rhodium compound.

Carbon monoxide, hydrogen and formaldehyde are readily available from numerous commercial sources. The molar ratios of these reactants which are suitable for use in the process of this invention will vary depending upon the reaction conditions. However, for general guidance, acceptable molar ratios of formaldehyde to carbon monoxide to hydrogen range from about 1:20:1 to about 1:1:20. Within this range, ratios of from about 1:20:1 to about 1:1:10 have been found to provide a preferred process.

The process is carried out at a temperature of from about 100° C. to about 200° C., preferably from about 120° C. to about 180° C. and a pressure of from about 1000 psi to about 10,000 psi, preferably from about 2000 psi to about 5000 psi.

In practice, the carbon monoxide and hydrogen reactants may be provided as a synthesis gas stream which is passed either co-currently or counter-currently to the formaldehyde reactant. In a preferred continuous embodiment a synthesis gas stream comprising carbon monoxide and hydrogen is passed counter-currently to a formaldehyde stream in cascade fashion so that the carbon monoxide is reacted out of the upward flowing stream.

The process employs an alcohol solvent and a catalyst comprising a rhodium compound. Suitable alcohols include, for example, methanol, ethanol, isobutanol and the like.

Rhodium is the catalyst for this process. It may be used in either the elemental rhodium metal or as a rhodium-containing compound. Rhodium exists in five oxidation states ranging from the zero state to the tetrapositive state. Of the positive oxidation states exhibited, the tripositive state is the most stable. Accordingly, the tripositive rhodium compounds are preferred. The oxides, halides and sulfates are examples of suitable rhodium tripositive compounds. The halo and cyano compounds and the amine complexes are also acceptable sources of rhodium.

Rhodium(III) oxide, $Rh_2O_3$ is an especially preferred rhodium compound. It is formed when powdered rhodium metal is heated in air above 600° C. Slow addition of alkali to solutions of tripositive rhodium results in the precipitation of the yellow hydrate $Rh_2O_3 \cdot 5H_2O$, which is also a preferred rhodium source.

Anionic complexes of tripositive rhodium with all the halogens are acceptable. Those with fluorine, chlorine, and bromine being particularly preferred. The anhydrous rhodium trihalides are representative halo compounds. They are obtained by appropriate direct union of the elements. The iodide can also be prepared by precipitation from aqueous solution. The trifluoride is a dark red substance, practically inert to water, acids and bases. The trichloride, as prepared by direct union, is also red and is insoluble in water and acids. Evaporation of a solution of rhodium(III) oxide hydrate in hydrochloric acid yields $RhCl_3 \cdot 4H_2O$. Removal of the water of crystallization at 180° C. in a hydrogen chloride atmosphere gives an anhydrous trichloride which is water-soluble; heating of this latter material to higher temperatures converts it to the water-insoluble form.

The rhodium sulfate hydrates are preferred sulfates. The best known are $Rh_2(SO_4)_3 \cdot 14H_2O$ and $Rh_2(SO_4)$-

$_3\cdot 6H_2O$. The former is a yellow material obtained by dissolving the oxide hydrate in cold dilute sulfuric acid and crystallizing by evaporation in vacuo at 0°; the red hexahydrate is prepared by evaporating an aqueous solution of the 14-hydrate to dryness at 100° C. From aqueous solutions of the 14-hydrate all the sulfate is immediately precipitated by addition of barium ion.

Cationic amine complexes of rhodium(III) are also suitable sources of rhodium. Representative compound types include, among others, $[Rh(NH_3)_6]X_3$, $[Rh(NH_3)_3]X_3$, $[Rh(NH_3)_5(H_2O)]X_3$, and $[Rh(NH_3)_5R]X_2$ (R=monovalent acid radical or OH-group) wherein X is a suitable anion, for example halide.

The following Examples further illustrate practice of the process of this invention. The Examples are representative and is not intended to limit the invention. Those familiar with the art will readily perceive modifications of the process in view of the Examples.

EXAMPLES

EXAMPLE I

A 300 cc Autoclave Engineers Magnedrive Autoclave was charged with 16 g of paraformaldehyde, 50 g of ethanol, and 0.2 g of $Rh_2O_3\cdot 5H_2O$. The autoclave was heated for 2 hours at 150° C. and at a pressure of 3300 psig using 67% $H_2$/33% CO. Vapor chromatographic analysis showed the product contained 2.8 g (8.8%) ethylene glycol and 12.74 g (79.6%) of methanol.

EXAMPLE II

The autoclave used in Example I was charged with 16 g of paraformaldehyde, 50 g of ethanol and 0.2 of $Rh_2O_3\cdot 5H_2O$. The reaction was run with 50% $H_2$/50% CO at 3000–3500 psig and 130° C. for 5 hours and another 6.5 hours at 3000–3300 psig and 150° C. The product contained 2.9 g (9% yield) of ethylene glycol and 2.9 g (18% yield) of methanol.

EXAMPLE III

The autoclave was charged with the same materials as in Example I and heated at 130° C. and 2400–2600 psig for four hours using 67% hydrogen/33% carbon monoxide. Vapor phase chromatographic analysis showed the presence of ethylal, ethylene glycol, and methanol as well as water and ethanol. Assuming all of the unreacted formaldehyde occurs as ethylal, the conversion of formaldehyde is 74% with selectivities of 35% for ethylene glycol and 46% for methanol. Unreacted formaldehyde in other forms (e.g. oligomers) not detected by vapor phase chromatography would give a lower conversion and higher selectivities.

EXAMPLE IV

The same materials as in Example III were heated at 130° C. and 2650–2750 psig for three hours giving a 56% conversion of formaldehyde with selectivities of 25% for ethylene glycol and 25% for methanol. It was assumed that all unreacted formaldehyde occurs as ethylal.

EXAMPLE V

The autoclave was charged with the same materials as in Example I and heated at 130° C. and 2900 psig for 4-½ hours using 50% hydrogen/50% carbon monoxide. Vapor phase chromatographic analysis, assuming all unreacted formaldehyde occurs as ethylal, gave a 62% conversion with selectivities of 13% for ethylene glycol and 16% for methanol.

In all of the above examples the vapor phase chromatograms show very little (less than about 7%) of other constituents in the reaction mixture.

What is claimed is:

1. A process for preparing ethylene glycol and methanol which comprises contacting formaldehyde, carbon monoxide, and hydrogen in the presence of an alcohol solvent and a catalytic amount of rhodium or a rhodium containing compound at a temperature of from about 100° C. to about 200° C. and a pressure of from about 1000 psi to about 10,000 psi wherein the molar ratio of formaldehyde to carbon monoxide to hydrogen is from about 1:20:1 to about 1:1:20.

2. A process according to claim 1 wherein said rhodium is a tripositive rhodium oxide.

3. A process according to claim 1 wherein the catalyst concentration is from about 0.1% to about 1%.

4. A process according to claim 1 wherein the temperature is from about 120° C. to about 180° C., the pressure is from about 2000 psi to about 5000 psi, and the catalyst comprises a tripositive rhodium oxide.

* * * * *